(12) United States Patent
Furukawa et al.

(10) Patent No.: US 6,414,181 B1
(45) Date of Patent: Jul. 2, 2002

(54) PROCESS OF PRODUCING CYCLOPROPANECARBOXYLATE COMPOUNDS

(75) Inventors: Takashi Furukawa, Osaka; Noritada Matsuo, Hyogo, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/477,804

(22) Filed: Jan. 5, 2000

(30) Foreign Application Priority Data

Jan. 7, 1999 (JP) .......................... 11-002156

(51) Int. Cl.[7] .................. C07C 69/74; C07U 61/04
(52) U.S. Cl. ........................... 560/124; 562/506
(58) Field of Search ..................... 560/124; 562/506

(56) References Cited

U.S. PATENT DOCUMENTS 3,009,946 A * 11/1961 Takei et al. ............ 260/468
4,024,163 A * 5/1977 Elliott et al. ............ 560/124
6,049,019 A * 4/2000 Fortunak et al. ......... 585/538

FOREIGN PATENT DOCUMENTS

JP          39-11369      *  6/1964  ............... 562/506

OTHER PUBLICATIONS

Paul R. Ortiz de Montellano et al: "Base–Catalyzed Isomerization of cis–and trans–2, 2–Dimethyl–3–formylcyclopropanecarboxylates. Nature of the Base–Stable Cis Intermediate", J. Org. Chem., vol. 43, pp 4323–4328 (1978).*
Makoto Fujita et al: "Practical, Sterocontrolled Synthesis of Polyfluorinated Artificial Pyrethroids", Bull. Chem. Soc. Jpn., vol. 60, pp 4385–4394 (1987).*
Matsui et al., Studies on Chrysanthemic Acid Part VIII, Agr. Biol. Chem., vol. 27, No. 5, p. 373–378, 1963.
Sugiyama et al., Chemical Studies on Pyrethroids Part II, Agr. Biol. Chem., vol. 36, No. 4, p. 565–569, 1972.
Tanaka et al., The Knoevenagel Reactions of Aldehydes with Carboxy Compounds, Bull. Chem. Soc. Jpn., 61, p. 2473–2479, 1988.
Lopez Aparicio et al., The Knoevenagel–Doebner Reaction in the Synthesis of Branched–Chain Sugar Derivatives, Carbohydrate Research, 103, p. 158–164, 1982.
Ma et al., Asymmetric Dipolar Cycloaddition Reactions: A Practical, Convergent Synthesis of Chiral Pyrrolidines, Tetrahedron: Asymmetry, vol. 8, No. 6, p. 883–887, 1997.

Smith et al., Cyclopropanes. V. Cyclopropyl Nitrocyclopropyl Ketones, and Their Behavior Toward Alkaline Reagents, Journal of American Chemical Society, vol. 73, p. 3831–3837, 1951.
Walter J. Gensler Et Al.: "Decarboxylative Condensation. Alpha–Alkylcinnamic Acids from Aromatic Aldehydes and Alkylmalonic Acids" Journal of the American Chemical Society., vol. 8, No. 18, Sep. 19, 1958, pp. 4949–4954, XP002134229, American Chemical Society, Washington, DC., US, ISSN: 0002–7863.

* cited by examiner

Primary Examiner—Paul J. Killos
(74) Attorney, Agent, or Firm—Fitch, Even, Tabin & Flannery

(57) ABSTRACT

Provided are processes of producing a cyclopropanecarboxylate compound of Formula (I):

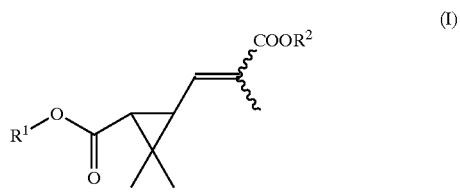

The processes comprise reacting a cyclopropanecarbaldehyde compound of Formula (II):

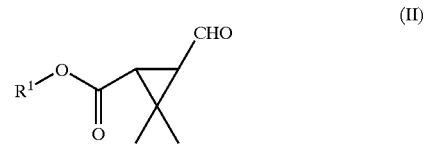

with a dicarboxylate compound of Formula (III):

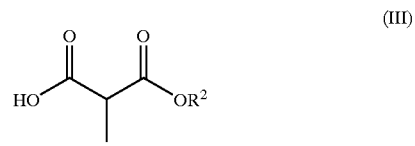

in the presence of at least one secondary amine from among piperidine, morpholine, pyrrolidine, diethylamine or N-methylethanolamine.

12 Claims, No Drawings

PROCESS OF PRODUCING CYCLOPROPANECARBOXYLATE COMPOUNDS

BACKGROUND OF THE INVENTION

1. Technical Field

The instant invention relates to methods of producing cyclopropanecarboxylic acid compounds.

2. Description of Related Art

Matsui et al. (Agric. Biol. and Chem., Vol. 27, pages 373 to 378, 1963) describes a process of producing a cyclopropanecarboxylic acid compound which is encompassed by the following reaction formula:

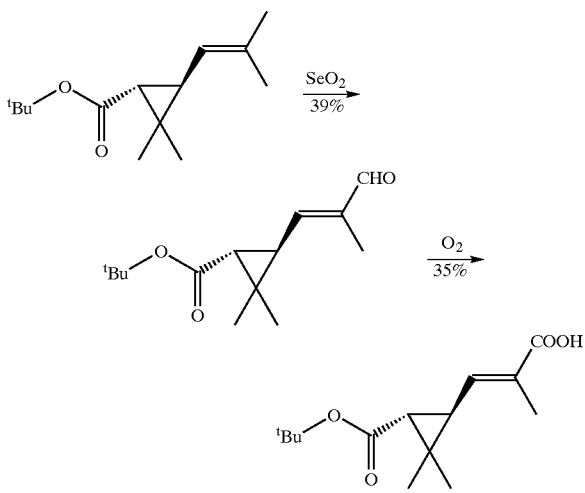

In the process described by Matsui et al., tert-butyl (±)-trans-2,2-dimethyl-3-[2-methyl-1-propenyl] cyclopropanecarboxylate is oxidized with the highly toxic corrosive compound of selenium dioxide to inadequately yield about 39% of a trans-aldehydic ester. Thereafter, said trans-aldehydic ester is oxidized with oxygen to yield about 35% of the cyclopropanecarboxylic acid compound. As such, the process described by Matsui et al. insufficiently yields about 14% of the cyclopropanecarboxylic acid compound. Further, the process needs troublesome work up operations of a poisonous selenium compound, which is a by-product from selenium dioxide.

Sugiyama et al. (Agric. Biol. and Chem., Vol. 36, pages 565 to 569, 1972) describes a process of producing a cyclopropanecarboxylic acid compound which is encompassed by the following reaction formula:

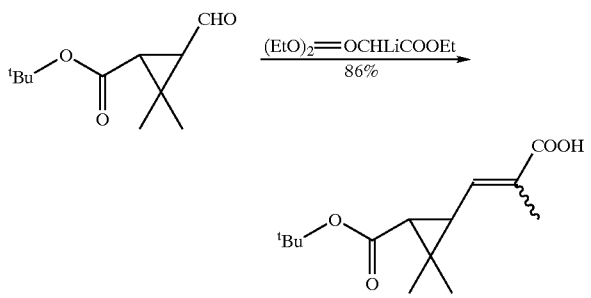

The process described by Sugiyama et al. utilizes the olefin synthesis of the Horner-Emmons reaction to yield about 86% of E and Z isomers of the cyclopropanecarboxylic acid compound. Such an olefin synthesis reaction also produces problematic phosphorous compounds, which often cause environmental problems when disposed with water sewage.

SUMMARY OF THE INVENTION

The instant invention provides efficient processes of producing cyclopropanecarboxylate compounds of the following formula (I):

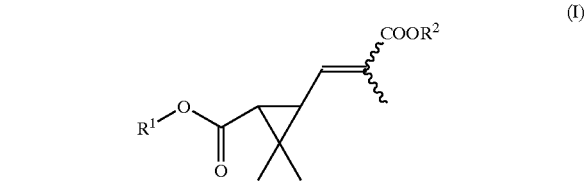

wherein, $R^1$ represents a hydrogen atom, $C_{1-5}$ alkyl group, $C_{1-5}$ haloalkyl group, $C_{1-3}$ alkoxy $C_{1-3}$ alkyl group, benzyl group, methoxybenzyl group, phenacyl group, 2-tetrahydrofuranyl group, 2-tetrahydropyranyl group or alcohol moiety of a pyrethroid compound and $R^2$ represents a hydrogen atom, $C_{1-10}$ alkyl group, $C_{1-10}$ haloalkyl group, $C_{3-10}$ alkenyl group, $C_{3-10}$ haloalkenyl group, $C_{3-10}$ alkynyl group, $C_{3-10}$ haloalkynyl group or benzyl group. Such processes efficiently produce the cyclopropanecarboxylate compounds by utilizing industrially easily available reagents to produce a high yield of the desired cyclopropanecarboxylate compounds of formula (I). In this regard, the processes of the instant invention avoid utilizing selenium dioxide or phosphorous compounds in producing said cyclopropanecarboxylate compounds, relative to the Horner-Emmons reaction or Matsui et al. process.

The instant invention fulfills to be efficient in producing cyclopropanecarboxylate compounds by providing a process which comprises reacting a cyclopropanecarbaldehyde compound of the following formula (II):

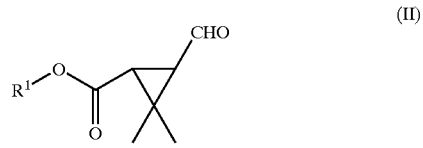

wherein $R^1$ represents the same as above, with a dicarboxylate compound of the following formula (III):

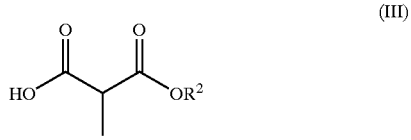

wherein $R^2$ represents the same as above, in the presence of at least one secondary amine chosen from piperidine, morpholine, pyrrolidine, diethylamine and N-methylethanolamine.

DETAILED DESCRIPTION OF THE INVENTION

The processes of the instant invention typically produce cyclopropanecarboxylate compounds which are encompassed by the following formula (I):

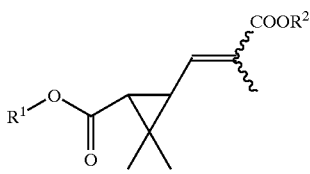

(I)

wherein, $R^1$ represents a hydrogen atom, $C_{1-5}$ alkyl group, $C_{1-5}$ haloalkyl group, $C_{1-3}$ alkoxy $C_{1-3}$ alkyl group, benzyl group, methoxybenzyl group, phenacyl group, 2-tetrahydrofuranyl group, 2-tetrahydropyranyl group or alcohol moiety of a pyrethroid compound and $R^2$ represents a hydrogen atom, $C_{1-10}$ alkyl group, $C_{1-10}$ haloalkyl group, $C_{3-10}$ alkenyl group, $C_{3-10}$ haloalkenyl group, $C_{3-10}$ alkynyl group, $C_{3-10}$ haloalkynyl group or benzyl group. Preferably, as $R^1$ in formula (I), the $C_{1-5}$ alkyl group is a methyl group, ethyl group, t-butyl group or the like, the $C_{1-5}$ haloalkyl group is a 2,2,2-trichloroethyl group, 2-chloroethyl group or the like, the $C_{1-3}$ alkoxy $C_{1-3}$ alkyl group is a methoxymethyl group, ethoxyethyl group or the like, the methoxybenzyl group is a p-methoxybenzyl group or the like, the alcohol moiety of a pyrethroid compound is a 3-phenoxybenzyl group, 5-benzyl-3-furylmethyl group, 2-methyl-4-oxo-3-(2-propynyl)-2-cyclopentenyl group, 2-methyl-4-oxo-3-(2-propenyl)-2-cyclopentenyl group, N-(3,4,5,6-tetrahydrophthalimido)methyl group, N-(3,4-dimethylmaleimido)methyl group or the like. $R^1$ is not limited thereto, but t-butyl is the most preferable group because the easiness of hydrolysis. Further, preferably as $R^2$ in formula (I), the $C_{1-10}$ alkyl group is a methyl group, ethyl group, n-propyl group, isopropyl group, n-butyl group, iso-butyl group, sec-butyl group or the like, the $C_{1-10}$ haloalkyl group is a 2,2,2-trifluoroethyl group, bis(trifluoromethyl)methyl group or the like, the $C_{3-10}$ alkenyl group is a 2-propenyl group or the like, the $C_{3-10}$ haloalkenyl group is a 3-chloro-2-propenyl group or the like, the $C_{3-10}$ alkynyl group is a 2-propynyl group or the like, the $C_{3-10}$ haloalkynyl group is a 3-iodo-2-propynyl group or the like, but $R^2$ is not limited thereto. The cyclopropanecarboxylate compounds of formula (I), which are produced by the processes of the instant invention, can be utilized as active ingredients of pesticides or to produce specified active ingredients of pesticides.

The processes of the instant invention react the cyclopropanecarbaldehyde compound of formula (II) with the dicarbonate compound of formula (III), in the presence of the specific secondary amine, namely piperidine, morpholine, pyrrolidine, diethylamine or N-methylethanolamine. The range of the reaction temperature for the reaction is usually 20 to 160° C., preferably 60 to 120° C. Further, the range of the reaction time period is usually 0.5 to 100 hours, preferably 1 to 72 hours.

In addition, the processes of the instant invention are usually performed within a solvent. Illustrative and non-limiting examples of the solvents include nitrogen-containing heterocycles such as pyridine and picoline; aliphatic hydrocarbons such as hexane, heptane, ligroin and petroleum ether; aromatic hydrocarbons such as benzene, toluene and xylene; halogenated hydrocarbons such as chlorobenzene and dichlorobenzene; ketones such as methyl isobutyl ketone; ethers such as diethyl ether, diisopropyl ether, 1,4-dioxane, tetrahydrofuran, ethylene glycol dimethyl ether and methyl t-butyl ether and the like. In the solvents above, pyridine and toluene are preferable, and pyridine is more preferable.

The amount of the dicarboxylate compound of formula (III) utilized in the instant processes is usually 1 to 10 moles, preferably 1 to 5 moles, based on 1 mole of the cyclopropanecarbaldehyde compound of formula (II), and the amount of the secondary amines described above is a catalytic amount to a large excess. The amount of said secondary amines depends on the kind of the utilized solvent, if a solvent is utilized, and it is usually 1 mole to a large excess based on 1 mole of the cyclopropanecarbaldehyde compound of formula (III) when a non-basic solvent is used. In cases that a basic solvent such as pyridine is used, said amount of secondary amines is usually 0.01 to 5 moles based on 1 mole of the cyclopropanecarbaldehyde compound of formula (II).

After reacting the cyclopropanecarbaldehyde compound of formula (II) and dicarboxylate compound of formula (III) in the presence of the secondary amine specified above, the cyclopropanecarboxylate compounds of formula (I) can be isolated therefrom by utilizing usual work up operations. Typical work up operations include concentration, addition of the reaction mixture to an aqueous solution containing an inorganic acid such as hydrochloric acid and sulfuric acid and extraction with an organic solvent.

It is also possible to obtain purer cyclopropanecarboxylate compounds of formula (I) from the crude product isolated in the above processes by employing well known purifying methods such as distillation, recrystallization or column chromatography.

Further, the utilized secondary amine and solvent can easily be collected and recycled after purification from the work up procedures by utilizing usual recovering procedures, such as by distilling separated organic phases resulting from the organic solvent extraction.

The cyclopropanecarbaldehyde compounds can be produced by various methods, but it is preferable to produce such compounds of formula (II) by utilizing methods which include an ozone oxidation reaction which is expressed by the following reaction formula (IV):

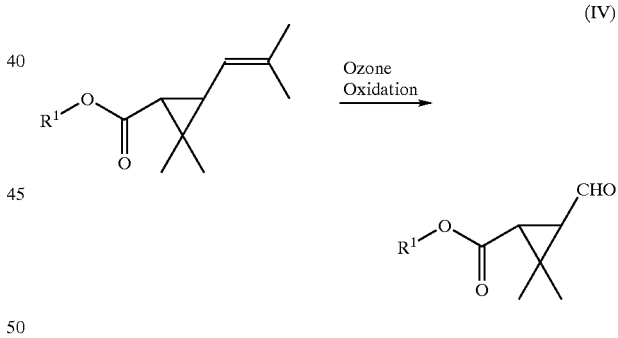

(IV)

Such an ozone oxidation reaction of formula (IV) is described in Bull. Chem. Soc.Jpn. (Vol. 60, pages 4385 to 4394, 1987) and J. Org. Chem. (Vol. 43, pages 4323 to 4328, 1978). After obtaining a cyclopropanecarbaldehyde compound of formula (II) wherein $R^1$ is a hydrogen atom, an esterification reaction is utilized to produce the cyclopropanecarbaldehyde compounds of formula (II). Said esterification reaction is expressed by the following reaction formula (V):

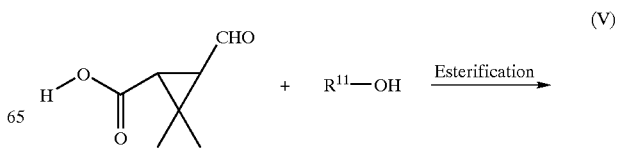

(V)

-continued

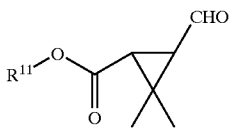

wherein $R^{11}$ represents a $C_{1-5}$ alkyl group, $C_{1-5}$ haloalkyl group, $C_{1-3}$ alkoxy $C_{1-3}$ alkyl group, benzyl group, methoxybenzyl group, phenacyl group, 2-tetrahydrofuranyl group, 2-tetrahydropyranyl group or an alcohol moiety of a pyrethroid. Such an esterification reaction of formula (V) is described in the J. Agric. Food Chem. (Vol. 43, pages 2286 to 2290, 1995).

The dicarboxylate compounds of formula (III) can be produced by various methods, but it is preferable to employ methods which include a hydrolysis reaction. For example, in order to produce the dicarboxylate compounds of formula (III), such a hydrolysis reaction may be expressed by the following reaction formula (VI):

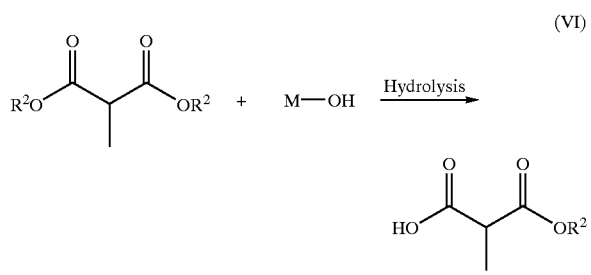

(VI)

wherein $R^2$ represents the same as defined above and M represents an alkali metal atom. Preferably, in reaction formula (VI), M represents a sodium atom or potassium atom.

EXAMPLES

Hereinafter, the instant invention is further explained through the following examples, but the instant invention is not limited thereto or thereby.

Example 1

Under a nitrogen atmosphere, 0.202 g of tert-butyl (±)-trans-2,2-dimethyl-3-formylcyclopropanecarboxylate was dissolved in 5 mL of anhydrous pyridine. One-fifth milliliter (0.20 mL) of piperidine and 0.242 g of methylmalonic acid was then added thereto, and the resulting mixture was stirred at a temperature of about 60° C. for a time period of about 1 hour. After the mixture was allowed to cool to room temperature, 100 mL of diethyl ether was added to said mixture and the resulting mixture was washed with 3N-hydrochloric acid and then saturated brine to obtain an organic layer therefrom. The organic layer was dried over anhydrous magnesium sulfate and thereafter the solvent was evaporated under reduced pressure in order to produce a residue. The residue was subjected to silica gel column chromatography, wherein the eluent was a mixture of n-hexane and ethyl acetate at a volume to volume ratio of 3:1 to give 0.249 g of tert-butyl (±)-trans-2,2-dimethyl-3-{2-carboxy-(E)-1-propenyl}cyclopropanecarboxylate.

Yield: 96%

$^1$H-NMR (CDCl$_3$ solvent, TMS as an inner standard, 270 MHz): δ values (ppm): 6.60 (dd, 1H), 2.14 (dd, 1H), 1.94 (d, 3H), 1.69 (d, 1H), 1.46 (s, 9h) 1.30 (s, 3H), 1.22 (s, 3H)

Example 2

Under a nitrogen atmosphere, 0.165 g of tert-butyl (±)-cis-2,2-dimethyl-3-formylcyclopropanecarboxylate was dissolved in 5 mL of anhydrous pyridine. Seventeen-hundredths milliliters (0.17 mL) of piperidine and 0.197 g of methylmalonic acid was then added thereto, and the resulting mixture was stirred at a temperature of 60° C. for a time period of 1 hour. After the mixture was allowed to cool to room temperature, 100 mL of diethyl ether was added to said mixture and the resulting mixture was washed with 3N-hydrochloric acid and then saturated brine to obtain an organic layer therefrom. The organic layer was dried over anhydrous magnesium sulfate and thereafter the solvent was evaporated under reduced pressure in order to produce a residue. The residue was subjected to silica gel column chromatography, wherein the eluent was a mixture of n-hexane and ethyl acetate at a volume to volume ratio of 3:1 to give 0.199 g of tert-butyl (±)-trans-2,2-dimethyl-3-{2-carboxy-(E)-1-propenyl}cyclopropanecarboxylate.

Yield: 94.1%

$^1$H-NMR (CDCl$_3$ solvent, TMS as an inner standard, 250 MHz): δ values (ppm): 6.60 (dd, 1H), 2.14 (dd, 1H), 1.94 (d, 3H), 1.69 (d, 1H), 1.46 (s, 9h), 1.30 (s, 3H), 1.22 (s, 3H)

Example 3

Under a nitrogen atmosphere, 0.306 g of tert-butyl (±)-trans-2,2-dimethyl-3-formyl-cyclopropanecarboxylate was dissolved in 3 mL of anhydrous pyridine. Two hundred sixty-three milligrams (0.263 mg) of piperidine and 0.352 g of ethyl methylmalonate was then added thereto, and the resulting mixture was stirred at a temperature of 100° C. for a time period of 5 hours. After the mixture was allowed to cool to room temperature, 100 mL of diethyl ether was added to said mixture and the resulting mixture was washed with 3N-hydrochloric acid and then saturated brine to obtain an organic layer therefrom. The organic layer was dried over anhydrous magnesium sulfate and thereafter the solvent was evaporated under reduced pressure in order to produce a residue. The residue was subjected to silica gel column chromatography, wherein the eluent solvent was a mixture of n-hexane and ethyl acetate at a volume to volume ratio of 3:1 to give 0.372 g of tert-butyl (±)-trans-2,2-dimethyl-3-{2-ethoxycarbonyl-(E)-1-propenyl}cyclopropanecarboxylate.

Yield: 85.1%

$^1$H-NMR (CDCl$_3$ solvent, TMS as an inner standard, 250 MHz): δ values (ppm): 6.45 (dd, 1H), 4.19 (q, 2H), 2.13 (dd, 1H), 1.94 (d, 3H), 1.65 (d, 1H), 1.46 (s, 9H), 1.30 (s, 3H), 1.28 (s, 3H), 1.23 (s, 3H)

Examples 4–7 and Reference Examples 1–7

General Procedure

Under a nitrogen atmosphere, 0.666 g of methyl (±)-trans-2,2-dimethyl-3-formylcyclopropanecarboxylate was dissolved in 10 mL of a designated solvent. A designated amount of an amine and 1.000 g of malonic acid was then added thereto, and the resulting mixture was stirred under heating. After the mixture was allowed to cool to room temperature, 50 mL of ethyl acetate was added to said mixture and the resulting mixture was washed with 3N-hydrochloric acid and then saturated brine to obtain an organic layer therefrom. The organic layer was dried over anhydrous magnesium sulfate and thereafter evaporated under reduced pressure in order to produce a residue. The residue was subjected to silica gel chromatography, wherein the eluent was a mixture of n-hexane and ethyl acetate at a volume to volume ratio of 3:1. Methyl(±)-trans-2,2-dimethyl-3-{2-carboxy-(E)-1-propenyl}cyclopropanecarboxylate was obtained.

$^1$H-NMR (CDCl$_3$ solvent, TMS as an inner standard, 250 MHz): δ values (ppm): 6.60 (dd, 1H), 3.70 (s, 3H), 2.22 (dd, 1H), 1.94 (d, 3H), 1.78 (d, 1H), 1.32 (s, 3H), 1.24 (s, 3H)

TABLE 1

| Run | Amines* | Reaction solvent | Temp. (C.) | Hours | Isolated yield (%) |
|---|---|---|---|---|---|
| Example 4 | piperidine, 0.025 | pyridine | 65 | 5 | 86.9 |
| Example 5 | piperidine, 0.95 | pyridine | 75 | 1 | 79.7 |
| Example 6 | morpholine, 1.06 | pyridine | 65 | 1 | 84.5 |
| Example 7 | pyrrolidine, 0.5 | pyridine | 65 | 1 | 70 |
| Example 8 | diethylamine, 0.92 | pyridine | 65 | 2.5 | 61.3 |
| Example 9 | N-methylethanolamine, 1.0 | pyridine | 65 | 2 | 74 |
| Example 10 | piperidine, 1.0 | pyridine | 70 | 1 | 83.7 |
| Ref. Ex. 1 | diisopropylamine, 1.3 | pyridine | 80 | 4 | 0 |
| Ref. Ex. 2 | dibutylamine, 1.0 | pyridine | 65 | 5.5 | 25.1 |
| Ref. Ex. 3 | dicyclohexylamine, 0.5 | pyridine | 65 | 2 | 0 |
| Ref. Ex. 4 | diisopropylethylamine, 0.51 | pyridine | 65 | 2 | 0 |
| Ref. Ex. 5 | 4-dimethylaminopyridine, 0.5 | pyridine | 65 | 2 | 0 |
| Ref. Ex. 6 | triethylamine, 1.5 | toluene | 80 | 5 | 11.1 |
| Ref. Ex. 7 | N,N-dimethlethanolamine, 0.5 | pyridine | 65 | 7 | 0 |

*the amount is a molar ratio based on the cyclopropanecarbaldehyde compound of formula (II).

What is claimed is:

1. A process of producing a cyclopropanecarboxylate compound of Formula (I):

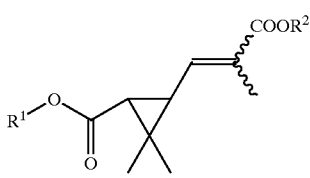

wherein, $R^1$ is a hydrogen atom, $C_{1-5}$ alkyl group, $C_{1-5}$ haloalkyl group, $C_{1-3}$ alkoxy $C_{1-3}$ alkyl group, benzyl group, methoxybenzyl group, phenacyl group, 2-tetrahydrofuranyl group, 2-tetrahydropyranyl group, or an alcohol moiety of a pyrethroid compound, and $R^2$ is a hydrogen atom, $C_{1-10}$ alkyl group, $C_{1-10}$ haloalkyl group, $C_{3-10}$ alkenyl group, $C_{3-10}$ haloalkenyl group, $C_{3-10}$ alkynyl group, $C_{3-10}$ haloalkynyl group, or benzyl group, said process comprising:

reacting a cyclopropanecarbaldehyde compound of Formula (II):

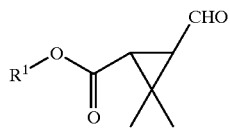

wherein $R^1$ is the same as above, with a dicarboxylate compound of Formula (III):

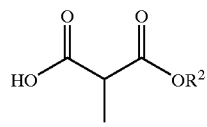

wherein $R^2$ is the same as above, in the presence of at least one secondary amine choosen from piperidine, morpholine, pyrrolidine, diethylamine and N-methylethanolamine.

2. The process according to claim 1, wherein as $R^1$, the $C_{1-5}$ alkyl group is a methyl group, ethyl group or t-butyl group, the $C_{1-5}$ haloalkyl group is a 2,2,2-trichloroethyl group or 2-chloroethyl group, the $C_{1-3}$ alkoxy $C_{1-3}$ alkyl group is a methoxymethyl group or ethoxyethyl group, the methoxybenzyl group is a p-methoxybenzyl group and the alcohol moiety of a pyrethroid compound is a 3-phenoxybenzyl group, 5-benzyl-3-furylmethyl group, 2-methyl-4-oxo-3-(2-propynyl)-2-cyclopentenyl group, 2-methyl-4-oxo-3-(2-propenyl)-2-cyclopentenyl group, N-(3,4,5,6-tetrahydrophthalimido)methyl group or N-(3,4-dimethylmaleimido)methyl group.

3. The process according to claim 1, wherein as $R^2$, the $C_{1-10}$ alkyl group is a methyl group, ethyl group, n-propyl group, iso-propyl group, n-butyl group, iso-butyl group or sec-butyl group, the $C_{1-10}$ haloalkyl group is a 2,2,2-trifluoroethyl group or bis(trifluoromethyl)methyl group, the $C_{3-10}$ alkenyl group is a 2-propenyl group, the $C_{3-10}$ haloalkenyl group is a 3-chloro-2-propenyl group, the $C_{3-10}$ alkynyl group is a 2-propynyl group, and the $C_{3-10}$ haloalkynyl group is a 3-iodo-2-propynyl group.

4. The process according to claim 1, wherein $R^2$ is a hydrogen atom.

5. The process according to claim 1, wherein the reaction is carried out at a temperature of from about 60 to 120° C.

6. The process according to claim 1, wherein the reaction is carried out in at least one solvent chosen from pyridine and toluene.

7. The process according to claim 6, wherein the reaction is carried out in pyridine.

8. The process according to claim 6, wherein the reaction is carried out in toluene.

9. The process according to claim 1, wherein $R^1$ represents a hydrogen atom, methyl or ethyl.

10. The process according to claim 9, wherein $R^1$ is methyl.

11. The processing according to claim 9, wherein $R^1$ is ethyl.

12. The process according to claim 9, wherein $R^1$ is a hydrogen atom.

* * * * *